US012767981B2

(12) United States Patent
Tadenuma et al.

(10) Patent No.: US 12,767,981 B2
(45) Date of Patent: Oct. 20, 2026

(54) NUCLEIC ACID SEQUENCE MEASUREMENT METHOD AND NUCLEIC ACID SEQUENCE MEASUREMENT KIT

(71) Applicant: Yokogawa Electric Corporation, Tokyo (JP)

(72) Inventors: Takashi Tadenuma, Musashino (JP); Yuki Miyauchi, Musashino (JP); Tomoyuki Taguchi, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 746 days.

(21) Appl. No.: 18/025,515

(22) PCT Filed: Aug. 27, 2021

(86) PCT No.: PCT/JP2021/031566
§ 371 (c)(1),
(2) Date: Mar. 9, 2023

(87) PCT Pub. No.: WO2022/059462
PCT Pub. Date: Mar. 24, 2022

(65) Prior Publication Data
US 2023/0323448 A1 Oct. 12, 2023

(30) Foreign Application Priority Data
Sep. 17, 2020 (JP) ................................ 2020-156555

(51) Int. Cl.
*C12Q 1/6874* (2018.01)

(52) U.S. Cl.
CPC ................................ *C12Q 1/6874* (2013.01)

(58) Field of Classification Search
None
See application file for complete search history.

(56) References Cited

U.S. PATENT DOCUMENTS 5,424,413 A * 6/1995 Hogan ................ C12Q 1/6823 536/24.31
6,020,132 A * 2/2000 Orum et al. ......... C12Q 1/6839 536/24.31
(Continued)

FOREIGN PATENT DOCUMENTS

JP 4482557 B2 6/2010
WO WO-9906595 A1 * 2/1999 ............ C12Q 1/682
(Continued)

OTHER PUBLICATIONS

Chan et al. Luminescent quantum dots for multiplexed biological detection and imaging. Current Opinion in Biotechnology 13:40-46 (2002). (Year: 2002).*
Extended European Search Report (EESR) dated Sep. 23, 2024 issued in European patent application No. 21869149.1.
(Continued)

*Primary Examiner* — Samuel C Woolwine
(74) *Attorney, Agent, or Firm* — RANKIN, HILL & CLARK LLP

(57) ABSTRACT

A target (50) having a specific nucleic acid sequence included in a sample is measured using a detection probe (10) that has a detection part having a nucleic acid sequence complementary to the nucleic acid sequence of the target (50), a label molecule A (20) having a nucleic acid sequence that is complementary to the nucleic acid sequence of the target (50) and different from the nucleic acid sequence of the detection part, and a label molecule B (30) having a nucleic acid sequence complementary to the nucleic acid sequence of the label molecule A (20), in which a fluorescent molecule is attached to either one of the label molecule A (20) and the label molecule B (30), and the label molecule A (20) and the label molecule B (30) bind to each other at least two or more sites to form a branched structural body of the label molecule A (20) and the label molecule B (30).

14 Claims, 3 Drawing Sheets

(56) References Cited

U.S. PATENT DOCUMENTS

| | | | | |
|---|---|---|---|---|
| 6,709,825 | B2 | 3/2004 | Mirkin et al. | |
| 8,658,361 | B2 * | 2/2014 | Wu | C12Q 1/6841 422/82.07 |
| 2003/0049631 | A1 | 3/2003 | Mirkin et al. | |
| 2004/0023207 | A1 * | 2/2004 | Polansky | A61K 48/005 435/456 |
| 2005/0130139 | A1 | 6/2005 | Usui et al. | |
| 2006/0160098 | A1 * | 7/2006 | Zak | C12Q 1/682 435/6.12 |
| 2007/0059752 | A1 * | 3/2007 | Cook | C07H 21/02 435/6.12 |
| 2008/0248963 | A1 | 10/2008 | Hakii et al. | |
| 2012/0172246 | A1 * | 7/2012 | Nguyen | C12Q 1/682 506/9 |
| 2020/0140921 | A1 * | 5/2020 | Fraser | C12Q 1/682 |
| 2022/0282300 | A1 * | 9/2022 | Pierce | C12Q 1/682 |

FOREIGN PATENT DOCUMENTS

| | | | |
|---|---|---|---|
| WO | 03/029441 | A1 | 4/2003 |
| WO | 2011038403 | A1 | 3/2011 |

OTHER PUBLICATIONS

He Hongfei et al: "Target-catalyzed autonomous assembly of dendrimer-like DNA nanostructures for enzyme-free and signal amplified colorimetric nucleic acids detection", Biosensors and Bioelectronics, vol. 86, Dec. 1, 2016 (Dec. 1, 2016), pp. 985-989.

Japanese Office Action (JPOA) dated Jun. 24, 2025 for Japanese Patent Application No. 2022-550438; English machine translation.

Microarray Protocols, Version 1, Dec. 21, 2007, total 14 pages, <URL:https://www.cvmbs.colostate.edu/microbiology/tb/pdf/arrays.pdf>.

Hirayama et al., "Development of DNA Chip for Detection of UGT1A1 Polymorphisms", Toyo Kohan, 2015, vol. 38, pp. 51-56, total 12 pages; Partial English translation.

* cited by examiner

NUCLEIC ACID SEQUENCE MEASUREMENT METHOD AND NUCLEIC ACID SEQUENCE MEASUREMENT KIT

TECHNICAL FIELD

The present invention relates to a nucleic acid sequence measurement method and a nucleic acid sequence measurement kit, each for measuring a target having a specific nucleic acid sequence included in a sample by hybridization.

BACKGROUND ART

As a method for measuring a target having a specific nucleic acid sequence included in a sample, a method using a DNA microarray (in which a detection probe having a sequence complementary to a specific nucleic acid sequence is provided on a solid-phase surface of a substrate or the like) is widely known. This method measures a target by utilizing a property whereby a target included in a sample added to a DNA microarray is captured by a detection probe of the DNA microarray by a hybridization reaction. In this method, the amount of the target included in the sample can be measured, in addition to examination as to whether the target is included in the sample. In Non-Patent Document 1 and Patent Document 1 below, a measurement method in the related art for measuring a target using a DNA microarray is disclosed.

CITATION LIST

Non-Patent Document

[Non-Patent Document 1]
Koichi Hirayama et al., Development of DNA Chip for Detection of UGT1A1 polymorphisms, Toyo Kohan Co., Ltd, Vol. 38, 51-56

Patent Document

[Patent Document 1]
Japanese Patent (Granted) Publication No. 4482557

DISCLOSURE OF INVENTION

Technical Problem

However, both of the methods disclosed in Non-Patent Document 1 and Patent Document 1 require a step of washing a DNA microarray before target detection. In the case of performing such washing, there is a problem in that the reproducibility of measurement results is deteriorated.

The present invention has been made in view of the above circumstances, and an object of the present invention is to provide a nucleic acid sequence measurement method and a nucleic acid sequence measurement kit, in which the reproducibility of measurement results of a target included in a sample is excellent by a simple step.

Solution to Problem

In order to achieve the object, the present invention adopts the following configurations.

[1] A nucleic acid sequence measurement method for measuring a target having a specific nucleic acid sequence included in a sample by hybridization, comprising:

(a) a step of adding a label molecule A into a sample solution including the target;

(b) a step of subjecting the target and the label molecule A to a hybridization reaction in the sample solution;

(c) a step of adding a label molecule B to the sample solution;

(d) a step of supplying the sample solution to a solid-phase surface of a substrate on which a detection probe is fixed;

(e) a step of subjecting the detection probe, the target, the label molecule A, and the label molecule B to a hybridization reaction;

(f) a step of separating an aggregate consisting of the target not binding to the detection probe, the label molecule A, and the label molecule B, and an aggregate consisting of the label molecule A and the label molecule B from the solid-phase surface; and (g) a step of irradiating the solid-phase surface with excitation light and measuring a quantity of fluorescence emitted from the solid-phase surface;

in which the detection probe has a detection part that is a sequence complementary to the nucleic acid sequence of the target, the label molecule A has a nucleic acid sequence complementary to the nucleic acid sequence of the target and different from the nucleic acid sequence of the detection part, the label molecule B has a nucleic acid sequence complementary to the nucleic acid sequence of the label molecule A, the label molecule A and the label molecule B bind to each other at at least two or more sites, and a fluorescent molecule is attached to a predetermined position of at least one of the label molecule A and the label molecule B.

[2] The nucleic acid sequence measurement method as described in [1], in which the label molecule A has a part x near the 3' end, a part y near the 5' end, and a part z that is a nucleic acid sequence complementary to the nucleic acid sequence of the target and different from the nucleic acid sequence of the detection part, the label molecule B has a part X near the 3' end and a part Y near the 5' end, the nucleic acid sequence of the part x is complementary to the nucleic acid sequence of the part X and the nucleic acid sequence of the part y is complementary to the nucleic acid sequence of the part Y, and two or more of either one or both of the parts x and the parts y are provided in the label molecule A; two or more of either one or both of the parts X and the parts Y are provided in the label molecule B; or two or more of either one or both of the parts x and the parts y are provided in the label molecule A and two or more of either one or both of the parts X and the parts Y are provided in the label molecule B.

[3] The nucleic acid sequence measurement method as described in [2], in which two or more of the parts y are provided in the label molecule A.

[4] The nucleic acid sequence measurement method as described in [2] or [3], in which two or more of the parts Y are provided in the label molecule B.

[5] The nucleic acid sequence measurement method as described in any one of [1] to [4], in which the predetermined position at which the fluorescent molecule is attached is in the middle of the label molecule A or the label molecule B.

[6] The nucleic acid sequence measurement method as described in any one of [1] to [5], in which the fluorescent molecules are attached to both of the label molecule A and the label molecule B.

[7] The nucleic acid sequence measurement method as described in any one of [1] to [5], in which a fine metal particle is attached to a predetermined position on either one of the label molecule A and the label molecule B.

[8] The nucleic acid sequence measurement method as described in [7], in which the predetermined position at which the fine metal particle is attached is in the middle of the label molecule A or the label molecule B.

[9] The nucleic acid sequence measurement method as described in any one of [1] to [8], in which the step of separating is performed by centrifugation.

[10] The nucleic acid sequence measurement method as described in any one of [1] to [9], in which the number of the hybridized target molecules is calculated from a change in the quantity of fluorescence before and after the hybridization reaction between the detection probe and the target, the label molecule A and the label molecule B.

[11] A nucleic acid sequence measurement kit for measuring a target having a specific nucleic acid sequence included in a sample by hybridization, comprising:

a detection probe having a detection part having a nucleic acid sequence complementary to a nucleic acid sequence of the target;

a substrate having a solid-phase surface on which the detection probe is fixed;

a label molecule A having a nucleic acid sequence complementary to the nucleic acid sequence of the target and different from the nucleic acid sequence of the detection part; and a label molecule B having a nucleic acid sequence complementary to the nucleic acid sequence of the label molecule A, in which the label molecule A and the label molecule B bind to each other at at least two or more sites, and a fluorescent molecule is attached to a predetermined position of at least one of the label molecule A and the label molecule B.

[12] The nucleic acid sequence measurement kit as described in [11], in which the label molecule A has a part x near the 3' end, a part y near the 5' end, and a part z that is a nucleic acid sequence complementary to the nucleic acid sequence of the target and different from the nucleic acid sequence of the detection part, the label molecule B has a part X near the 3' end and a part Y near the 5' end, the nucleic acid sequence of the part x is complementary to the nucleic acid sequence of the part X and the nucleic acid sequence of the part y is complementary to the nucleic acid sequence of the part Y, and two or more of either one or both of the parts x and the parts y are provided in the label molecule A; two or more of either one or both of the parts X and the parts Y are provided in the label molecule B; or two or more of either one or both of the parts x and the parts y are provided in the label molecule A and two or more of either one or both of the parts X and the parts Y are provided in the label molecule B.

[13] The nucleic acid sequence measurement kit as described in [12], in which two or more of the parts y are provided in the label molecule A.

[14] The nucleic acid sequence measurement kit as described in [12] or [13], in which two or more of the parts Y are provided in the label molecule B.

[15] The nucleic acid sequence measurement kit as described in any one of [11] to [14], in which the predetermined position at which the fluorescent molecule is attached is in the middle of the label molecule A or the label molecule B.

[16] The nucleic acid sequence measurement kit as described in any one of [11] to [15], in which the fluorescent molecules are attached to both of the label molecule A and the label molecule B.

[17] The nucleic acid sequence measurement kit as described in any one of [11] to [15], in which a fine metal particle is attached to a predetermined position on either one of the label molecule A and the label molecule B.

[18] The nucleic acid sequence measurement kit as described in [17], in which the predetermined position at which the fine metal particle is attached is in the middle of the label molecule A or the label molecule B.

Advantageous Effects of Invention

According to the present invention, there is an effect that a nucleic acid sequence measurement method and a nucleic acid sequence measurement kit, each of which is excellent in the reproducibility of the measurement results of a target included in a sample by a simple step, can be provided.

BEST MODE FOR CARRYING OUT THE INVENTION

Figure 1:
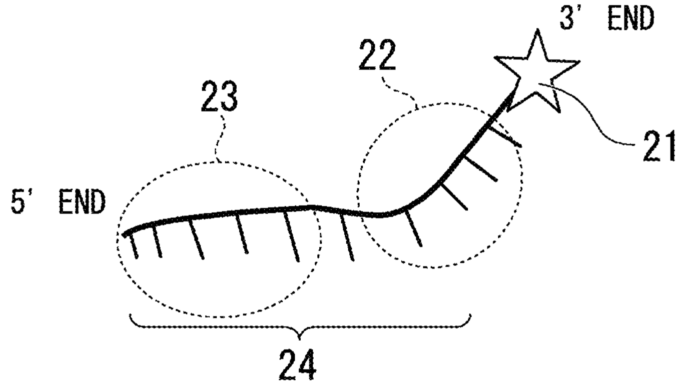
FIG. 1 is a diagram showing a configuration example of a label molecule A.

Hereinafter, the nucleic acid sequence measurement method and the nucleic acid sequence measurement kit according to embodiments of the present invention will be described in detail with reference to the drawings. Hereinbelow, a summary of the embodiments of the present invention will first be described, and then details of the embodiments of the present invention will be described.

SUMMARY

The embodiments of the present invention are intended to improve the reproducibility of measurement results of a target included in a sample by a simple step. The above-mentioned Non-Patent Document 1 discloses a method for detecting a target in a sample by adding a fluorescence-modified PCR product obtained by subjecting a DNA sample to PCR using a fluorescence-modified primer to a DNA microarray to perform a hybridization reaction. Moreover, the above-mentioned Patent Document 1 discloses a method for increasing the quantity of detected light by labeling a large number of fluorescent molecules as means for increasing the quantity of detected light.

However, in the method disclosed in the above-mentioned Non-Patent Document 1, the process is complicated because a modification of a DNA sample serving as a target with a fluorescent molecule is required, and a step of washing a DNA microarray prior to detection is required. In addition, depending on the method for washing the DNA microarray, a decrease in signal or an increase in the quantity of background light may occur, or uneven washing may cause uneven signal in a solid-phase surface. These are factors which reduce the reproducibility of the measurement results. In addition, in the method of Patent Document 1, washing the solid-phase surface before detection is required, and as in the above-mentioned Non-Patent Document 1, there is a problem of a reduction in reproducibility of measurement results associated with the washing.

In the target measurement method of the present embodiment, first, a label molecule A is added to a sample solution including a target, and the target and the label molecule A are subjected to a hybridization reaction. Next, a label molecule B is added to the sample solution. Subsequently, the sample solution is supplied to a solid-phase surface of a substrate on which a detection probe is fixed, and the detection probe, the target, label molecule A, and the label molecule B are subjected to a hybridization reaction. Subsequently, an aggregate consisting of the target not binding to the detection probe, the label molecule A, and the label molecule B, and an aggregate consisting of the label molecule A and the label molecule B are separated from the solid-phase surface. Then, the solid-phase surface is irradiated with fluorescence and the quantity of fluorescence emitted from the solid-phase surface is measured.

Here, the detection probe has a detection part that is a sequence complementary to the nucleic acid sequence of the target. In addition, the label molecule A has a nucleic acid sequence complementary to the nucleic acid sequence of the target and different from the nucleic acid sequence of the detection part, and the label molecule B has a nucleic acid sequence complementary to the nucleic acid sequence of the label molecule A. The label molecule A and the label molecule B bind to each other at at least two or more sites, and a fluorescent molecule is attached to a predetermined position of at least one of the label molecule A and the label molecule B.

As a result, it is possible to improve the reproducibility of the measurement results of the target included in the sample by a simple step. Specifically, in addition to eliminating the need of a labeling step for a nucleic acid serving as a target, it is possible to prevent a deterioration in performance, a decrease in the quantity of light, an increase in background light, an occurrence of variations, and the like due to an inadequate washing step by omitting a washing step before a detection step. With methods in the related art, there is a risk of an increase in signal and background light, and variations due to the washing method, the washing degree, uneven washing, and the like, but such a risk can be avoided by the present invention. As a result, more uniform results can be obtained on a surface of an array and the reproducibility of detection is also improved. In addition, it is possible to increase a quantity of detected light by increasing the number of fluorescent molecules that bind to the detection probe hybridized with the target, whereby the detection sensitivity is improved.

EMBODIMENTS

<Nucleic Acid Sequence Measurement Method>

The nucleic acid sequence measurement method of the present invention is a nucleic acid sequence measurement method for measuring a target having a specific nucleic acid sequence included in a sample by hybridization, including:

(a) a step of adding a label molecule A into a sample solution including the target;

(b) a step of subjecting the target and the label molecule A to a hybridization reaction in the sample solution;

(c) a step of adding a label molecule B to the sample solution;

(d) a step of supplying the sample solution to a solid-phase surface of a substrate on which a detection probe is fixed;

(e) a step of subjecting the detection probe, the target, the label molecule A, and the label molecule B to a hybridization reaction;

(f) a step of separating an aggregate consisting of the target not binding to the detection probe, the label molecule A, and the label molecule B, and an aggregate consisting of the label molecule A and the label molecule B from the solid-phase surface; and (g) a step of irradiating the solid-phase surface with excitation light and measuring a quantity of fluorescence emitted from the solid-phase surface;

in which the detection probe has a detection part that is a sequence complementary to the nucleic acid sequence of the target, the label molecule A has a nucleic acid sequence complementary to the nucleic acid sequence of the target and different from the nucleic acid sequence of the detection part, the label molecule B has a nucleic acid sequence complementary to the nucleic acid sequence of the label molecule A, the label molecule A and the label molecule B bind to each other at at least two or more sites, and a fluorescent molecule is attached to a predetermined position of at least one of the label molecule A and the label molecule B.

The label molecule A has a part x near the 3' end, a part y near the 5' end, and a part z that is a nucleic acid sequence complementary to the nucleic acid sequence of the target and different from the nucleic acid sequence of the detection part, the label molecule B has a part X near the 3' end and a part Y near the 5' end, the nucleic acid sequence of the part x is complementary to the nucleic acid sequence of the part X and the nucleic acid sequence of the part y is complementary to the nucleic acid sequence of the part Y.

Furthermore, in the present invention, a term of "complementary" means having nucleic acid sequences where one nucleic acid sequence and another nucleic acid sequence can form a double-stranded state, and it is not necessary that the nucleic acid sequences be completely complementary and several mismatched base pairs may be included.

The part x is located near the 3' end of the label molecule A and is located several bases from the 3' end of the label molecule A.

The part y is located near the 5' end of the label molecule A and is located several bases from the 5' end of the label molecule A.

The part X is located near the 3' end of the label molecule B and is located several bases from the 3' end of the label molecule B.

The part Y is located near the 5' end of the label molecule B and is located several bases from the 5' end of the label molecule B.

In the label molecule A, the part z may or may not overlap all or a part of the part x or the part y.

By allowing the label molecule A to have a part z that is a nucleic acid sequence complementary to the nucleic acid sequence of the target and different from the nucleic acid sequence of the detection part, the target binding to the part z of the label molecule A can bind to the detection part of the detection probe fixed on a solid phase surface.

Two or more of either one or both of the parts x and the parts y are provided in the label molecule A; two or more of either one or both of the parts X and the parts Y are provided in the label molecule B; or two or more of either one or both of the parts x and the parts y are provided in the label molecule A and two or more of either one or both of the parts X and the parts Y are provided in the label molecule B. For example, two or more of the parts y may be provided in the label molecule A; two or more of the parts Y may be provided in the label molecule B; and two or more of the parts y may be provided in the label molecule A and two or more of the parts Y may be provided in the label molecule B.

Since the nucleic acid sequence of the part x is complementary to the part X and the nucleic acid sequence of the part y is complementary to the part Y, the part x of the label molecule A binds to the part X of the label molecule B and the part y of the label molecule A binds to the part Y of the label molecule B. As a result, a structure having repeating branched structures from a plurality of the label molecules A and the label molecules B is formed.

A fluorescent molecule is attached to a predetermined position of at least one of the label molecule A and the label molecule B. The fluorescent molecule may not be attached to a tip end of the label molecule A or the label molecule B, and may be located in the middle of the label molecule A or the label molecule B. In addition, a plurality of types of fluorescent molecules may be added at a plurality of sites. By attaching the fluorescent molecules to a plurality of sites, the quantity of fluorescence during detection can be increased and detection with a higher sensitivity can be performed.

The fluorescent molecule is not particularly limited as long as it can be attached to a predetermined position of at least one of the label molecule A and label molecule B, and examples thereof include known fluorescent molecules such as EDANS, Coumarin, FAM, FITC, Cy2 (registered trademark), TF2, TF3, HEX, JOE, TET, Cy3 (registered trademark), Cy5 (registered trademark), Alexa Fluor (registered trademark) 532, Alexa Fluor (registered trademark) 610, Alexa Fluor (registered trademark) 647, ATTO532, ATTO633, Qdot (registered trademark) 565, Qdot (registered trademark) 585, Qdot (registered trademark) 605, Qdot (registered trademark) 705, iFluor™ 532, and iFluor™ 647

FIG. 1 is a diagram showing an example of the structure of the label molecule A. In FIG. 1, the label molecule A has one part x 22 and one part y 23, and a fluorescent molecule 21 is attached to the 3' end.

Figure 2:
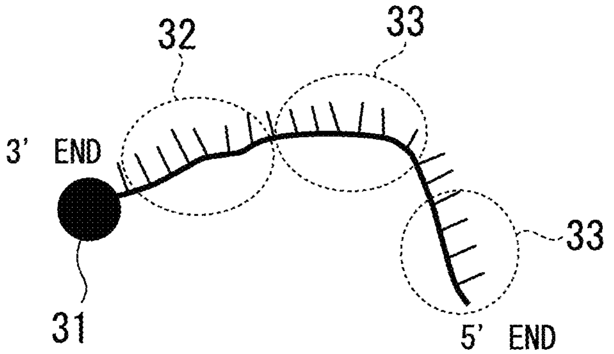
FIG. 2 is a diagram showing a configuration example of a label molecule B.

FIG. 2 is a diagram showing an example of the structure of the label molecule B. In FIG. 2, the label molecule B has one part X 32 and two parts Y 33, and a fine metal particle 31 is attached to the 5' end.

Figure 3:
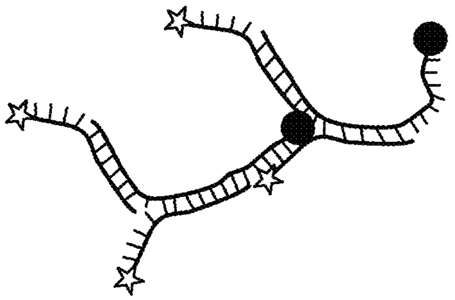
FIG. 3 is a diagram showing a structure having repeating branched structures formed from a label molecule A and a label molecule B binding to each other.

FIG. 3 shows a state where the label molecule A shown in FIG. 1 and the label molecule B shown in FIG. 2 are bound. The part x of the label molecule A binds to the part X of the label molecule B, and the part y of the label molecule A binds to the part Y of the label molecule B. As a result, as shown in FIG. 3, a structure having repeating branched structures from a plurality of the label molecules A and the label molecules B is formed.

The fluorescent molecule may be attached to both of the label molecule A and the label molecule B. By attaching the fluorescent molecule to both of the label molecule A and the label molecule B, it is possible to increase the quantity of fluorescence during detection.

A fine metal particle may be attached to a predetermined position of either one of the label molecule A and the label molecule B. By attaching the fine metal particle to either one of the label molecule A and the label molecule B, the label molecule A and the label molecule B bind to each other to form an aggregate having a branched structure, and weight can be added to the aggregate. Therefore, separation is facilitated by centrifugation. In addition, since magnetism can be imparted to the aggregates, the aggregates can be separated by magnetic force. The fine metal particle may be attached to a tip end of the label molecule A or the label molecule B, or may be attached to a position in the middle of the label molecule A or the label molecule B. In addition, a plurality of types of fine metal particles may be added at a plurality of sites. By attaching the fine metal particles at a plurality of sites, the weight or the magnetism of the aggregate can be increased, whereby separation can be facilitated by centrifugation or magnetic force.

The fine metal particle is not particularly limited as long as it can be attached to a predetermined position on either label molecule A or label molecule B, and examples thereof include a gold nanoparticle, a silver nanoparticle, iron oxide, and a black silica particle. The particle diameter of the fine metal particle is preferably such that the fine metal particles are highly dispersible in a solution, do not interfere with a hybridization reaction between DNAs, and have a density or mass that allows sedimentation by centrifugation. In order to achieve a high dispersibility in a solution, the iron oxide particle preferably has a particle diameter of 100 nm or less, and the gold nanoparticle preferably has a particle diameter of 15 nm or less, but in order not to interfere with the hybridization reaction between DNAs, a smaller particle diameter is preferable.

Figure 4:
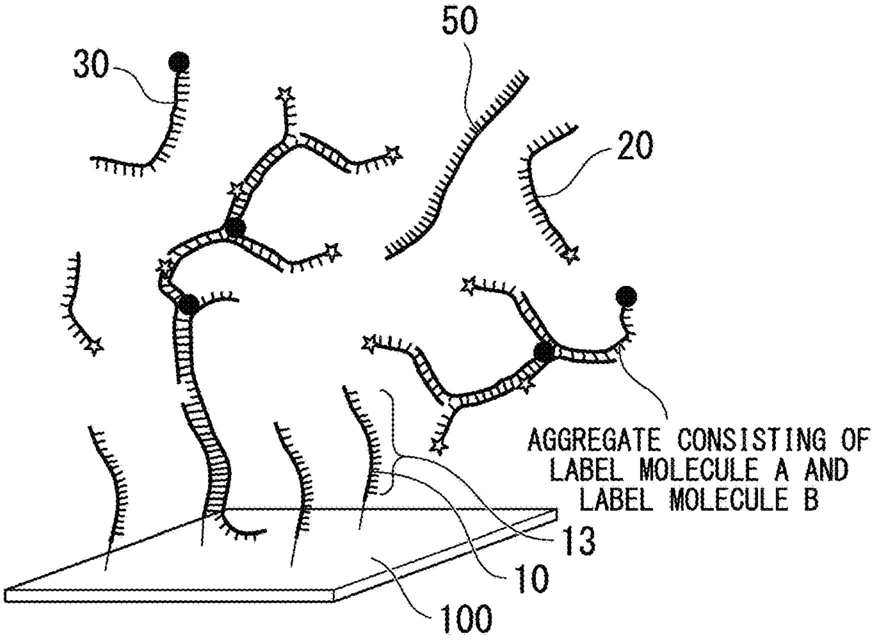
FIG. 4 is a diagram schematically showing the detection of a target.

Each of the steps will be described below. FIG. 4 is a diagram schematically showing the principle of the nucleic acid sequence measurement method of the present invention.

First, preparation of a sample solution including a target 50 having a desired specific nucleic acid sequence is performed. Amplification of a nucleic acid (target 50) having a specific nucleic acid sequence may be performed in the preparation of the sample solution.

A test may be performed to confirm whether or not a gene is amplified at the gene amplification stage, and only in the case where the gene is amplified may a hybridization reaction be performed, as described later.

Furthermore, the timing for examining the presence or absence of the gene is not limited to being made after completion of amplification, and may be made during the amplification reaction. Electrophoresis, an antigen-antibody reaction, mass spectrometry, real-time PCR, or the like can be appropriately used as the examination method.

In addition, the nucleic acid (target 50) may be bound to a protein, a sugar chain, or the like. In this case, an interaction of the protein, the sugar chain, or the like with the nucleic acid (target 50) can be confirmed.

A label molecule A (20) is added to a sample solution including the target 50 (step (a)). Thereafter, the target 50 and the label molecule A (20) are hybridized with each other in the sample solution including the target 50 (step (b)).

In the case where the target 50 and the label molecule A (20) are subjected to a hybridization reaction in the sample solution including the target 50, the target 50 binds to a part z 24 of the label molecule A (20).

After subjecting the target 50 and the label molecule A (20) to the hybridization reaction, a label molecule B (30) is added to the sample solution including the target 50 and the label molecule A (20) (step (c)). Thereafter, a solution obtained by adding the label molecule B (30) to the sample solution including the target 50 and the label molecule A (20) is supplied to a solid-phase surface 100 on which a detection probe 10 is fixed (step (d)).

Next, the detection probe 10, the target 50, the label molecule A (20), and the label molecule B (30) are subjected to a hybridization reaction (step (e)). In the case where the detection probe 10, the target 50, the label molecule A (20), and the label molecule B (30) are subjected to the hybridization reaction, the part x 22 of the label molecule A (20) binding to the target 50 in the step (b) binds to the part X 32 of the label molecule B (30) and the part y 23 of the label molecule A (20) binding to the target 50 binds to the part Y 33 of the label molecule B (30). As a result, a branched structural body having repeating branched structures from a plurality of the label molecules A (20) and the label molecules B (30) is formed, a structural body consisting of the target 50, the label molecule A (20), and the label molecule B (30) having the target 50 binding to the above-mentioned branched structural body is formed, and the target 50 of the structural body binds to a detection part 13 of the detection probe 10 fixed on the solid-phase surface 100.

In the step (b), also for the label molecule A (20) not binding to the target 50, the part x 22 of the label molecule A (20) binds to the part X 32 of the label molecule B (30) and the part y 23 of the label molecule A (20) binds to the part Y 33 of the label molecule B (30). As a result, a branched structural body having repeating branched structures from a plurality of the label molecules A (20) and the label molecules B (30) is formed, and an aggregate consisting of the label molecule A (20) and label molecule B (30) is formed and exists in a free state in the solution.

Next, an aggregate consisting of the target 50 not binding to the detection probe 10, the label molecule A (20), and the label molecule B (30), and an aggregate consisting of the label molecule A (20) and the label molecule B (30) are separated from the solid-phase surface 100 (step (f)). As a method for separating the aggregates from the solid-phase surface 100, centrifugation is preferable. The aggregate consisting of the target 50 not binding to the detection probe 10, the label molecule A (20), and the label molecule B (30), and the aggregate consisting of the label molecule A (20) and the label molecule B (30) can be separated from the solid-phase surface 100 by centrifugation. In addition, in the case where the fine metal particle 31 is attached to either one of the label molecule A (20) and the label molecule B (30), the aggregate consisting of the target 50 not binding to the detection probe 10, the label molecule A (20), and the label molecule B (30), and the aggregate consisting of the label molecule A (20) and the label molecule B (30) can be separated by magnetic force. In the step (f), since the aggregate consisting of the target 50 not binding to the detection probe 10, the label molecule A (20), and the label molecule B (30), and the aggregate consisting of the label molecule A (20) and the label molecule B (30) can be removed without washing, a quantity of light can be measured without an influence of the washing.

Next, the solid-phase surface 100 is irradiated with excitation light, and fluorescence from the solid-phase surface 100 is measured by a fluorescence reading apparatus 60 (step (g)).

The presence or absence of the target nucleic acid (target 50) in the sample can be confirmed by examining whether or not the detection probe 10 exhibits fluorescence with the fluorescence reading apparatus 60, and the hybridized target nucleic acid (target 50) can be quantified.

In addition, by using the fluorescence reading apparatus 60, it is possible to acquire images before and after the hybridization at the same coordinates while acquiring fluorescence images separated by wavelength at the time, and by analyzing the fluorescence images, it is also possible to calculate the number of molecules of the target 50 that have undergone the hybridization reaction.

In addition, the number of molecules of the target 50 that have undergone the hybridization reaction can be calculated from a quantity of fluorescence variation of the fluorescent molecule 21 before and after the hybridization reaction. For example, the hybridization reaction is performed using a standard solution of the target 50 having a known number of molecules, the quantity of fluorescence variation of the fluorescent molecule 21 before and after the reaction is measured, and a calibration curve showing a relationship between the number of molecules and the quantity of fluorescence variation is created in advance. From this calibration curve and the quantity of fluorescence variation of the fluorescent molecule 21 before and after the hybridization reaction using a sample, it is possible to calculate the number of molecules of the target 50 that have undergone the hybridization reaction.

The solid-phase surface on which a detection probe is fixed is not limited to a flat surface on a substrate. The detection probe may be fixed on the surface of a bead. By fixing a detection probe on the surface of a bead, the detection probe has a shape that spreads radially around the bead. In this case, the surface area of the solid-phase surface on which the probes are fixed is increased, and the number of probes per unit area can be increased. In addition, it is possible to selectively recover molecules to be detected by recovering the beads that have captured the molecules to be detected by size, magnetism, or the like thereof. The recovered molecules can be used for other tests in subsequent steps.

Nucleic Acid Sequence Measurement Kit

Next, the nucleic acid sequence measurement kit of the present invention will be described. The nucleic acid sequence measurement kit of the present invention can be used for the nucleic acid sequence measurement method of the present invention.

The nucleic acid sequence measurement kit of the present embodiment includes the detection probe 10 having the detection part 13 having a nucleic acid sequence complementary to the nucleic acid sequence of the target 50 that is a nucleic acid to be detected, a substrate having the solid-phase surface 100 on which the detection probe 10 is fixed, the label molecule A having a nucleic acid sequence complementary to the nucleic acid sequence of the target 50 and different from the nucleic acid sequence of the detection part 13, and the label molecule B having a nucleic acid sequence complementary to the nucleic acid sequence of the label molecule A. The label molecule A and the label molecule B bind to each other at at least two or more sites, and the fluorescent molecule 21 is attached to a predetermined position of at least one of the label molecule A and the label molecule B. Examples of the fluorescent molecule 21 include those described above.

As shown in FIG. 1, the label molecule A has the part x 22 near the 3' end, the part y 23 near the 5' end, and the part z 24 that is a nucleic acid sequence complementary to the nucleic acid sequence of the target 50 and different from the nucleic acid sequence of the detection part 13. As shown in FIG. 2, the label molecule B has the part X 32 near the 3' end and the part Y 33 near the 5' end. The nucleic acid sequence of the part x 22 is complementary to the nucleic acid sequence of the part X 32 and the nucleic acid sequence of the part y 23 is complementary to the nucleic acid sequence of the part Y 33.

The part x 22 is located near the 3' end of the label molecule A and is located several bases from the 3' end of the label molecule A.

The part y 23 is located near the 5' end of the label molecule A and is located several bases from the 5' end of the label molecule A.

The part X 32 is located near the 3' end of the label molecule B and located several bases from the 3' end of the label molecule B.

The part Y 33 is located near the 5' end of the label molecule B and located several bases from the 5' end of the label molecule B.

In the label molecule A, the part z 24 may or may not overlap all or a part of the part x 22 or the part y 23.

By allowing the label molecule A to have the part z 24 that is a nucleic acid sequence complementary to the nucleic acid sequence of the target 50 and different from the nucleic acid sequence of the detection part 13, the target 50 binding to the part z 24 of the label molecule A can bind to the detection part 13 of the detection probe 10 fixed on the solid-phase surface 100 of the substrate.

Two or more of either one or both of the part x 22 and the part y 23 are provided in the label molecule A; two or more of either one or both of the part X 32 and the part Y 33 are provided in the label molecule B; or two or more of either one or both of the part x 22 and the part y 23 are provided in the label molecule A and two or more of either one or both of the part X 32 and the part Y 33 are provided in the label molecule B. For example, two or more of the part y 23 may be provided in the label molecule A; two or more of the part Y 33 may be provided in the label molecule B; and two or more of the part y 23 may be provided in the label molecule A and two or more of the part Y 33 may be provided in the label molecule B.

Since the nucleic acid sequence of the part x 22 is complementary to the part X 32 and the nucleic acid sequence of the part y 23 is complementary to the part Y 33, the part x 22 of the label molecule A binds to the part X 32 of the label molecule B and the part y 23 of the label molecule A binds to the part Y 33 of the label molecule B. As a result, a structure having repeating branched structures from a plurality of the label molecules A and the label molecules B is formed.

The fluorescent molecule 21 is attached to a predetermined position of at least one of the label molecule A and the label molecule B. The fluorescent molecule 21 may not be attached to a tip end of the label molecule A or the label molecule B, or may be located in the middle of the label molecule A or the label molecule B. In addition, a plurality of types of fluorescent molecules 21 may be added at a plurality of sites. By attaching the fluorescent molecules 21 to a plurality of sites, the quantity of fluorescence during detection can be increased and a detection with a higher sensitivity can be performed.

The fluorescent molecules 21 may be attached to both of the label molecule A and the label molecule B. By attaching the fluorescent molecules 21 to both of the label molecule A and the label molecule B, it is possible to increase the quantity of fluorescence during detection.

The fine metal particle 31 may be attached to a predetermined position of either one of the label molecule A and the label molecule B. By attaching the fine metal particle 31 to either one of the label molecule A and the label molecule B, the label molecule A and the label molecule B bind to each other to form an aggregate having a branched structure, and weight can be added to the aggregate. Therefore, separation is facilitated by centrifugation. In addition, since magnetism can be imparted to the aggregates, the aggregates can be separated by magnetic force. The fine metal particle 31 may be attached to a tip end of the label molecule A or the label molecule B, or may be attached to a position in the middle of the label molecule A or the label molecule B. In addition, a plurality of types of the fine metal particles 31 may be added at a plurality of sites. By attaching the fine metal particles 31 at a plurality of sites, the weight or the magnetism of the aggregate can be increased, whereby separation can be facilitated by centrifugation or magnetic force. Examples of the fine metal particles 31 include those described above.

The nucleic acid sequence measurement kit of the present invention may further include a standard solution necessary for quantifying a target, a necessary buffer solution, instructions, and the like.

Method for Using Nucleic Acid Sequence Measurement Kit

Next, a method for using the nucleic acid sequence measurement kit of the present invention will be described.

(1) Preparation of Solution

First, a probe solution including the detection probe 10 is prepared and the probe concentration is adjusted.

(2) Fixation onto Solid-Phase Surface

Next, the probe solution is spotted on a solid-phase surface 100 of a substrate to fix the detection probe 10 on the solid-phase surface 100 of the substrate.

(3) Washing

Next, the solid-phase surface 100 is washed to remove excess unfixed probes. Through the procedure, a substrate having the solid-phase surface 100 on which the detection probe is fixed is produced.

(4) Preparation of Sample Solution

Next, preparation of a sample solution including a target 50 having a desired specific nucleic acid sequence is performed. Amplification of a nucleic acid (target 50) having a specific nucleic acid sequence may be performed in the preparation of the sample solution.

(5) Hybridization Reaction Between Target and Label Molecule A

Next, the label molecule A (20) is added to the sample solution including the target 50 prepared in (4). Thereafter, the target 50 and the label molecule A (20) are subjected to a hybridization reaction in the sample solution including the target 50. In the case where the target 50 and the label molecule A (20) are subjected to a hybridization reaction in the sample solution including the target 50, the target 50 binds to a part z 24 of the label molecule A (20).

(6) Hybridization Reaction Among Detection Probe, Target, Label Molecule A, and Label Molecule B After the target 50 and the label molecule A (20) are subjected to a hybridization reaction, a label molecule B (30) is added to the sample solution including the target 50 and the label molecule A (20). Thereafter, a solution obtained by adding the label molecule B (30) to the sample solution including the target 50 and the label molecule A (20) prepared in (4) is supplied to a substrate having a solid-phase surface 100 on which the detection probe 10 is fixed, and the detection probe 10 fixed on the solid-phase surface 100, the target 50, the label molecule A (20), and the label molecule B (30) are subjected to a hybridization reaction. In the case where the detection probe 10 fixed on the solid-phase surface 100, the target 50, the label molecule A (20), and the label molecule B (30) are subjected to a hybridization reaction, the part x 22 of the label molecule A (20) binding to the target 50 binds to the part X 32 of the label molecule B (30) and the part y 23 of the label molecule A (20) binding to the target 50 binds to the part Y 33 of the label molecule B (30). As a result, a branched structural body having repeating branched structures from a plurality of the label molecules A (20) and the label molecules B (30) is formed, a structural body consisting of the target 50, the label molecule A (20), and the label molecule B (30), in which the target 50 binds to the branched structural body, is formed, and the target 50 of the structural body binds to the detection part 13 of the detection probe 10 fixed on the solid-phase surface 100.

(7) Separation and Removal of Aggregates

Next, an aggregate consisting of the target 50 not binding to the detection probe 10, the label molecule A (20), and the label molecule B (30), and an aggregate consisting of the label molecule A (20) and the label molecule B (30) are separated from the solid-phase surface 100. As a method for separating the aggregates from the solid-phase surface 100, centrifugation is preferable. In the case where the fine metal particle 31 is attached to either one of the label molecule A (20) and the label molecule B (30), an aggregate consisting of the target 50 not binding to the detection probe 10, the label molecule A (20), and the label molecule B (30), and an aggregate consisting of the label molecule A (20) and the label molecule B (30) can be separated by magnetic force, in addition to centrifugation.

(8) Detection of Fluorescence

Next, the solid-phase surface 100 in which the target 50, the label molecule A (20), and the label molecule B (30) bind to the detection probe 10 is irradiated with excitation light, and fluorescence emitted from the solid-phase surface 100 is detected with the fluorescence reading apparatus 60.

The presence or absence of the target nucleic acid (target 50) in the sample can be confirmed by examining whether or not the detection probe 10 exhibits fluorescence with the fluorescence reading apparatus 60, and the hybridized target nucleic acid (target 50) can be quantified.

In addition, by using the fluorescence reading apparatus 60, it is possible to acquire images before and after the hybridization at the same coordinates while acquiring fluorescence images separated by wavelength at the time, and by analyzing the fluorescence images, it is also possible to calculate the number of molecules of the target 50 that have undergone the hybridization reaction.

In addition, the number of molecules of the target 50 that have undergone the hybridization reaction can be calculated from a quantity of fluorescence variation of the fluorescent molecule 21 before and after the hybridization reaction. For example, the hybridization reaction is performed using a standard solution of the target 50 having a known number of molecules, the quantity of fluorescence variation of the fluorescent molecule 21 before and after the reaction is measured, and a calibration curve showing a relationship between the number of molecules and the quantity of fluorescence variation is created in advance. From this calibration curve and the quantity of fluorescence variation of the fluorescent molecule 21 before and after the hybridization reaction using a sample, it is possible to calculate the number of molecules of the target 50 that have undergone the hybridization reaction.

Figure 5:
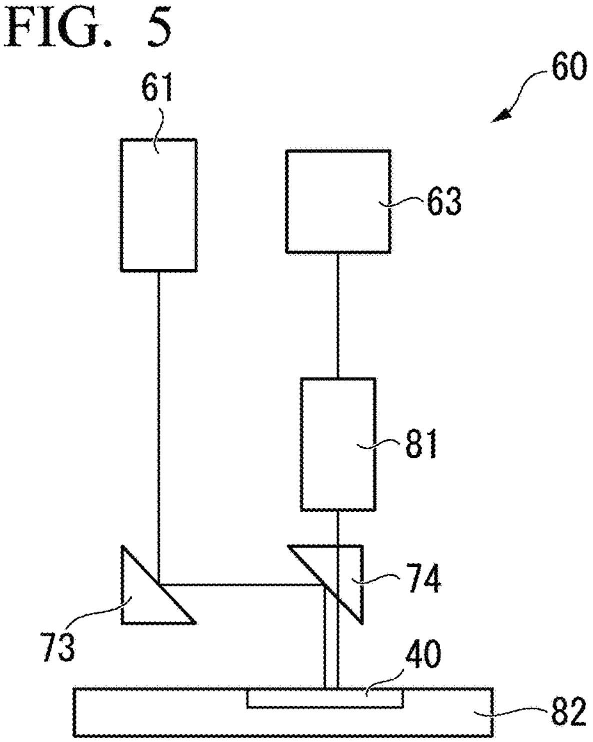
FIG. 5 is a configuration diagram showing a fluorescence reading apparatus.

FIG. 5 is a configuration diagram showing the fluorescence reading apparatus 60. In order to acquire images before and after the hybridization of the target 50 of a DNA chip 40 with the detection probe 10 with the fluorescence reading apparatus 60, an image before hybridization is acquired, then the temperature of the DNA chip 40 is then raised by a temperature control stage 82 to allow a hybridization reaction to proceed, and an image is acquired after the hybridization in a state where the temperature is lowered to room temperature again.

The temperature control stage 82 preferably has functions of shaking, rotating the DNA chip 40, and stirring with a vortex mixer or the like during the reaction between the target 50 and the detection probe 10 in order to accelerate the hybridization between the target 50 and the detection probe 10.

In an optical system of the fluorescence reading apparatus 60, laser light emitted from a laser light source 61 is reflected by a mirror 73 to a dichroic mirror 74, and the DNA chip 40 is irradiated with the laser light. The irradiated light turns into an excitation light for the fluorescent molecule 21 on the DNA chip 40, and in the case where the wavelength of the laser light source 61 and the excitation wavelength of the fluorescent molecule 21 overlap, the fluorescent molecule 21 is in an excitation state.

The fluorescence emitted from the DNA chip 40 is transmitted through the dichroic mirror 74, passes through an imaging optical system 81, and forms an image on a detection element of a CCD camera 63, whereby the fluorescence is detected. Here, to prevent the excitation light from leaking into the detected light, a band-pass filter matched to an excitation light wavelength may be installed on the excitation light side, and a band-pass filter matched to a fluorescence wavelength to be detected may also be installed on the detected light side.

For a fluorescence image obtained by the fluorescence reading apparatus 60, images before and after the hybridization reaction between the target 50 and the detection probe 10 in the same spot can be acquired. Therefore, the fluorescence image is not affected by variations in the quantity of light between solid phases and between spots. In addition, fluorescence variation can be calculated from the fluorescence images before and after the hybridization reaction, and the number of molecules that have undergone the binding reaction can be calculated. The quantity of fluorescence variation may be calculated using an average quantity of light in all spots, or using the quantity of fluorescence variation for each pixel of the spot image.

The fluorescence reading apparatus 60 may be provided with a computer that controls the CCD camera 63, an arithmetic device that calculates the quantity of light of an image, and a recording apparatus that stores an image, the quantity of light, and the like.

The scope of application of the present invention is not intended to be limited to the embodiments. The present invention can be widely applied to a nucleic acid sequence measurement method for measuring a target having a specific nucleic acid sequence included in a sample by hybridization, and a nucleic acid sequence measurement kit using the nucleic acid sequence measurement method.

EXAMPLES

Hereinafter, the present invention will be described in more detail with reference to Examples, but is not limited to the following Examples.

PCR amplification was performed using a genomic DNA extracted from a *Staphylococcus aureus* strain (NBRC12732) as a template and a primer capable of amplifying a 16S rDNA region. The obtained PCR-amplified product was diluted to a DNA concentration of 20 nM and used as a sample solution.

Figure 6:
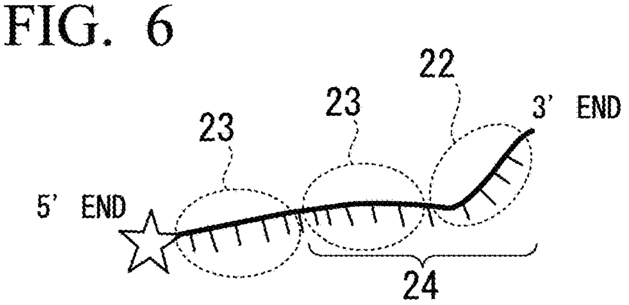
FIG. 6 is a diagram showing the structure of a label molecule A used in Examples.

Next, a label molecule A shown in FIG. 6 was added to the sample and incubated at 65° C. for 1 hour to allow the PCR-amplified product and the label molecule A to bind to each other. Furthermore, as shown in FIG. 6, the label molecule A used in the present Example was modified at the 5' end with a fluorescent molecule Cy3 (registered trademark) and had one part x and two parts y, and the part x and the parts y constituted parts z.

Figure 7:
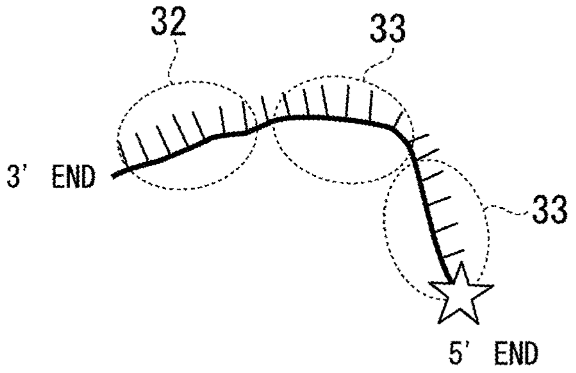
FIG. 7 is a diagram showing the structure of a label molecule B used in Examples.

Next, the label molecule B shown in FIG. 7 was added to the sample solution, and then supplied to a microarray in which a plurality of detection probes were provided on a solid-phase surface of a substrate, and incubated at 60° C. for 3 hours. Furthermore, as shown in FIG. 7, the label molecule B used in the present Example was modified with Cy3 (registered trademark) at the 5' end and had one part X and two parts Y.

Figure 8:
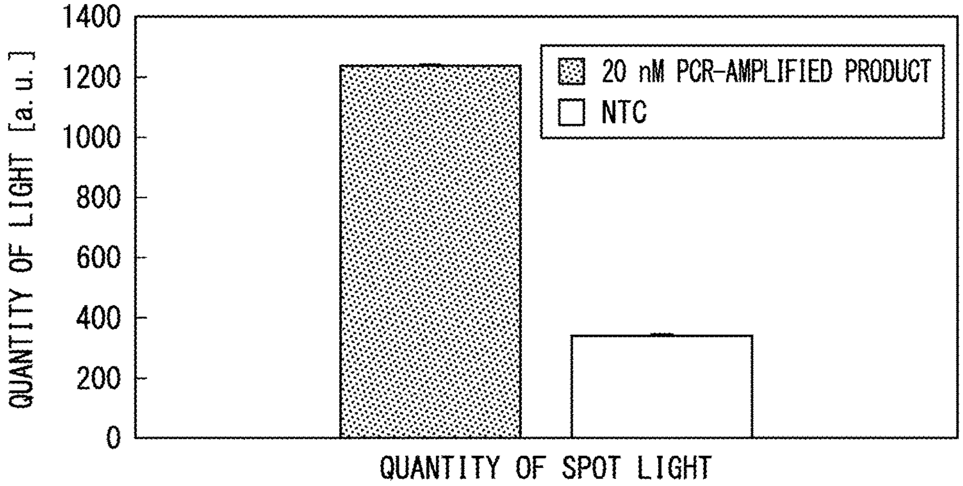
FIG. 8 is a diagram showing the quantities of spot light in the case where a sample including a target and a sample not including a target are subjected to a hybridization reaction in Examples.

Then, the microarray was centrifuged at 3,000 g in a centrifuge to sediment aggregates not binding to the detection probes. After the centrifugation, the quantity of spot light was measured using a fluorescence reading apparatus. In addition, as a negative control, a solution including a genomic DNA (non-target control; hereinafter referred to as NTC) extracted from *Escherichia coli* that does not bind to an amplifiable primer for the 16S rDNA region was used as a sample solution and subjected to the same procedure above, and the quantity of spot light was measured. The results are shown in FIG. 8. As shown in FIG. 8, a significant increase in fluorescence was confirmed from the PCR-amplified product of a genomic DNA of *Staphylococcus aureus* strain, compared to NTC.

Figure 9:
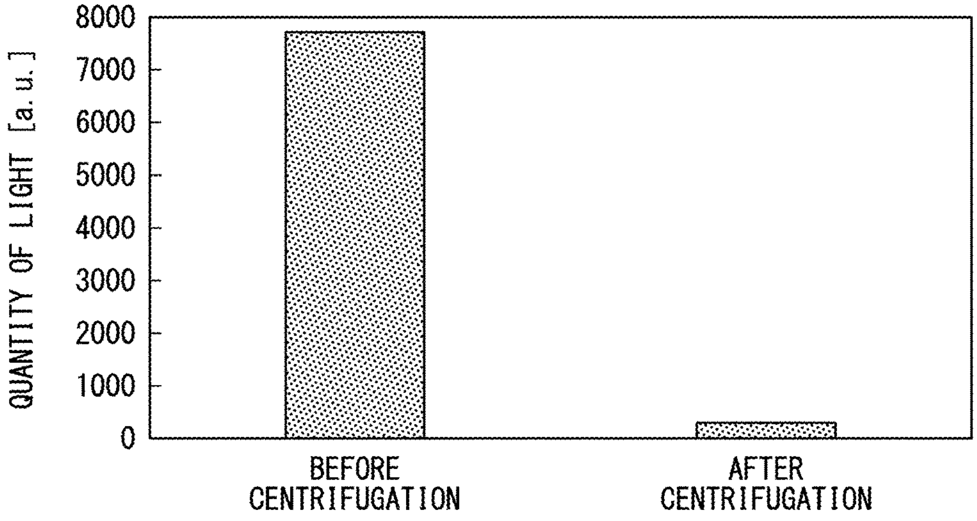
FIG. 9 is a diagram showing the quantities of background light of a solution before and after centrifugation of a microarray in Examples.

FIG. 9 shows the quantity of background light before and after microarray centrifugation. As shown in FIG. 9, the background light could be reduced to 5% or less by microarray centrifugation.

From the results above, it was confirmed that the nucleic acid sequence measurement method of the present invention is capable of detecting a target while not requiring a step of modifying a target nucleic acid by fluorescence and a step of washing a solid phase before detection, and the detection sensitivity is excellent.

REFERENCE SIGNS LIST

10: Detection probe
13: Detection part
20: Label molecule A
21: Fluorescent molecule
22: Part x
23: Part y
24: Part z
30: Label molecule B
31: Fine metal particle
32: Part X
33: Part Y
40: DNA chip
50: Target
60: Fluorescence reading apparatus
61: Laser light source
63: CCD camera
73: Mirror
74: Dichroic mirror
81: Imaging optical system
82: Temperature control stage
100: Solid-phase surface

The invention claimed is:

1. A nucleic acid sequence measurement method for measuring a target having a specific nucleic acid sequence included in a sample by hybridization, comprising:

(a) a step of adding a label molecule A into a sample solution including the target;

(b) a step of subjecting the target and the label molecule A to a hybridization reaction to form a complex of the target and the label molecule A in the sample solution;

(c) a step of adding a label molecule B to the sample solution;

(d) a step of supplying the sample solution to a solid-phase surface of a substrate on which a detection probe is fixed;

(e) a step of subjecting the complex of the target and the label molecule A to a hybridization reaction with the label molecule B and the detection probe;

(f) a step of separating an aggregate consisting of the target not binding to the detection probe, the label molecule A, and the label molecule B, and an aggregate consisting of the label molecule A and the label molecule B from the solid-phase surface; and (g) a step of irradiating the solid-phase surface with excitation light and measuring a quantity of fluorescence emitted from the solid-phase surface;

wherein the detection probe has a detection part that is a sequence complementary to the nucleic acid sequence of the target, the label molecule A has a nucleic acid sequence complementary to the nucleic acid sequence of the target and different from the nucleic acid sequence of the detection part, the label molecule B has a nucleic acid sequence complementary to the nucleic acid sequence of the label molecule A, the label molecule A and the label molecule B bind to each other at at least two or more sites, and a fluorescent molecule is attached to a predetermined position of both of the label molecule A and the label molecule B, wherein the label molecule A has a part x near the 3' end, a part y near the 5' end, and a part z that is a nucleic acid sequence complementary to the nucleic acid sequence of the target and different from the nucleic acid sequence of the detection part, the label molecule B has a part X near the 3' end and a part Y near the 5' end, the nucleic acid sequence of the part x is complementary to the nucleic acid sequence of the part X and the nucleic acid sequence of the part y is complementary to the nucleic acid sequence of the part Y, and two or more of either one or both of the parts x and the parts y are provided in the label molecule A and two or more of either one or both of the parts X and the parts Y are provided in the label molecule B.

2. The nucleic acid sequence measurement method according to claim 1, wherein two or more of the parts y are provided in the label molecule A.

3. The nucleic acid sequence measurement method according to claim 1, wherein two or more of the parts Y are provided in the label molecule B.

4. The nucleic acid sequence measurement method according to claim 1, wherein the predetermined position at which the fluorescent molecule is attached is in the middle of the label molecule A or the label molecule B.

5. The nucleic acid sequence measurement method according to claim 1, wherein a fine metal particle is attached to a predetermined position on either one of the label molecule A and the label molecule B.

6. The nucleic acid sequence measurement method according to claim 5, wherein the predetermined position at which the fine metal particle is attached is in the middle of the label molecule A or the label molecule B.

7. The nucleic acid sequence measurement method according to claim 1, wherein the step of separating is performed by centrifugation.

8. The nucleic acid sequence measurement method according to claim 1, wherein the number of the hybridized target molecules is calculated from a change in the quantity of fluorescence before and after the hybridization reaction between the detection probe and the target, the label molecule A and the label molecule B.

9. A nucleic acid sequence measurement kit for measuring a target having a specific nucleic acid sequence included in a sample by hybridization, comprising:

a detection probe having a detection part having a nucleic acid sequence complementary to a nucleic acid sequence of the target;

a substrate having a solid-phase surface on which the detection probe is fixed;

a label molecule A having a nucleic acid sequence complementary to the nucleic acid sequence of the target and different from the nucleic acid sequence of the detection part; and a label molecule B having a nucleic acid sequence complementary to the nucleic acid sequence of the label molecule A, wherein the label molecule A and the label molecule B bind to each other at at least two or more sites, and a fluorescent molecule is attached to a predetermined position of both of the label molecule A and the label molecule B, wherein the label molecule A has a part x near the 3' end, a part y near the 5' end, and a part z that is a nucleic acid sequence complementary to the nucleic acid sequence of the target and different from the nucleic acid sequence of the detection part, the label molecule B has a part X near the 3' end and a part Y near the 5' end, the nucleic acid sequence of the part x is complementary to the nucleic acid sequence of the part X and the nucleic acid sequence of the part y is complementary to the nucleic acid sequence of the part Y, and two or more of either one or both of the parts x and the parts y are provided in the label molecule A and two or more of either one or both of the parts X and the parts Y are provided in the label molecule B.

10. The nucleic acid sequence measurement kit according according to claim 9, wherein two or more of the parts y are provided in the label molecule A.

11. The nucleic acid sequence measurement kit according according to claim 9, wherein two or more of the parts Y are provided in the label molecule B.

12. The nucleic acid sequence measurement kit according to claim 9, wherein the predetermined position at which the fluorescent molecule is attached is in the middle of the label molecule A or the label molecule B.

13. The nucleic acid sequence measurement kit according to claim 9, wherein a fine metal particle is attached to a predetermined position on either one of the label molecule A and the label molecule B.

14. The nucleic acid sequence measurement kit according to claim 13, wherein the predetermined position at which the fine metal particle is attached is in the middle of the label molecule A or the label molecule B.

* * * * *